US006881543B2

(12) United States Patent
Philpott et al.

(10) Patent No.: US 6,881,543 B2
(45) Date of Patent: Apr. 19, 2005

(54) SAMPLING AND STORAGE SYSTEM FOR GENETIC MATERIAL FROM TISSUE

(75) Inventors: Richard Philpott, Elsworth (GB); Martin A. Smith, Brookline, MA (US); Frank D. Igoe, Walpole, MA (US); James C. Davis, Kingston, MA (US)

(73) Assignee: Whatman, Inc., Newton, MA (US)

( * ) Notice: Subject to any disclaimer, the term of this patent is extended or adjusted under 35 U.S.C. 154(b) by 54 days.

(21) Appl. No.: 09/993,736

(22) Filed: Nov. 14, 2001

(65) Prior Publication Data

US 2002/0081618 A1 Jun. 27, 2002

Related U.S. Application Data

(60) Provisional application No. 60/248,876, filed on Nov. 15, 2000.

(51) Int. Cl.[7] ........................... C12Q 1/68; C07H 21/04
(52) U.S. Cl. ........................ 435/6; 435/2; 435/4; 435/5; 435/174; 536/23.1; 536/24.3
(58) Field of Search ............................... 435/6, 5, 91.1, 435/91.2, 2, 4, 174; 536/23.1, 24.3

(56) References Cited

U.S. PATENT DOCUMENTS

| | | | | |
|---|---|---|---|---|
| 5,143,627 A | | 9/1992 | Lapidus et al. ............. | 210/767 |
| 5,496,562 A | | 3/1996 | Burgoyne ................... | 424/488 |
| 5,756,126 A | | 5/1998 | Burgoyne ................... | 424/488 |
| 5,807,527 A | | 9/1998 | Burgoyne ................... | 422/488 |
| 5,811,061 A | | 9/1998 | Martinson et al. .......... | 122/102 |
| 5,972,386 A | | 10/1999 | Burgoyne ................... | 424/488 |
| 6,054,277 A | | 4/2000 | Furcht et al. .................. | 435/6 |
| 6,153,104 A | * | 11/2000 | Robertson ................... | 210/650 |
| 6,187,540 B1 | * | 2/2001 | Staub et al. .................... | 435/6 |
| 6,503,747 B1 | * | 1/2003 | Kathariou et al. ........ | 435/252.3 |
| 2001/0000149 A1 | * | 4/2001 | Smith et al. .................... | 435/6 |

OTHER PUBLICATIONS

Gibco BRL Products Catalog (FTA Card, p. 2–7, 1999).*
Alberts, et al. Molecular Biology of the Cell. 3$^{rd}$ Edition. pp. 308–313, 1994.*
P. Natarajan, et al., "Paper–Based Archiving of Mammalian and Plant Samples for RNA Analysis"*BioTechniques*, 2000:29: 1328–1333.

J. Higgins, et al., "Detection of Francisella Tularensis in Infected Mammals and Vectors using a Probe–Based Polymerase Chain Reaction", *Am. J. Trop. Med. Hyg.: 2000:* 62(2): 310–318.
K. Hsiao, et al., "Application of FTA Sample Collection and DNA Purification System on the Determination of CTG Trinucleotide Repeat Size by PCT–Base Southern Blotting," *Journal of Clinical Laboratory Analysis*, 1999:13: 188–193.
Del Rio et al., "Reusing the Same Blood–stained Punch for Sequential DNA Amplifications and Typing," *BioTechniques*,1996:20(6): 970, 972, 974.
K. Rogers and L. Burgoyne, "Bacterial Typing: Storing and Processing of Stabilized Reference Bacteria for Polymerase Chain Reaction without Preparing DNA–An Example of an Automatable Procedure", *Analytical Biochemistry*, 1997: 247: 223–227.
M. Ibrahim et al., "Real–Time Microchip PCR for Detecting Single–Base Differences in Viral and Human DNA", *Analytical Chemistry*, 1998: 70: 2013–2017.
L. Ledray and L. Netzel, "DNA Evidence Collection", *The Journal of Emergency Nursing 1997*:23 (2 156–158.
P. Belgrader et al., "Automated DNA Purification and Amplification from Blood–Stained Cards Using a Robotic Workstation", *BioTechniques*, 1995: 19 (3): 426,428,430, 432.
H. Baron et al., "Oligonucleotide Ligation assay (OLA) for the diagnosis of familial hypercholesterolemia," *Nature Biotechnology*, 1996: 14: 1279–1282.
P. Belgrader et al., "Automated Sample Processing Using Robotics for Genetic Typing of Short Tandem Repeat Polymorphisms by Capillary Electrophoresis", *Laboratory Robotics and Automation* 1997: 9:3–7.

* cited by examiner

*Primary Examiner*—Jeanine A. Goldberg
(74) *Attorney, Agent, or Firm*—David G. Conlin; Kathryn A. Piffat; Edwards & Angell, LLP

(57) ABSTRACT

The invention relates to methods, a kit, and an apparatus for detecting and analyzing genetic material from a biological sample. The method can be used to analyze samples from a wide variety of sources, including tissues, blood, plasma, sera, mucus, urine, saliva, sweat, semen, and cultures, as well as analyzing samples of contaminated water, food, beverages, and other items.

33 Claims, 1 Drawing Sheet

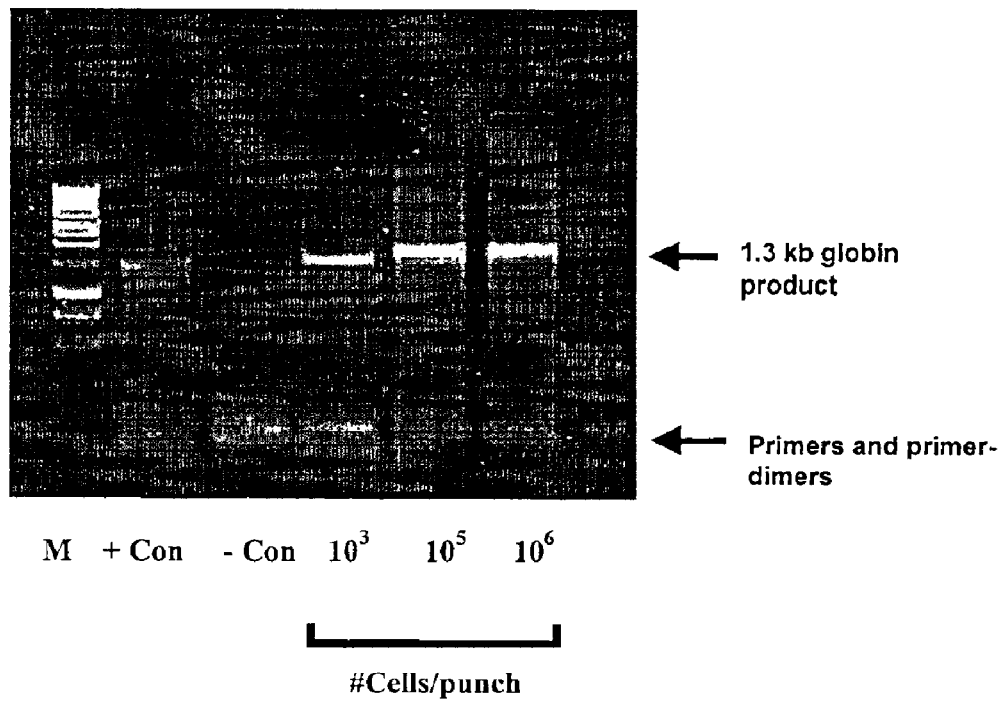

SAMPLING AND STORAGE SYSTEM FOR GENETIC MATERIAL FROM TISSUE

CROSS-REFERENCE TO RELATED APPLICATION

This application claims priority of U.S. Provisional Application Ser. No. 60/248,876, filed Nov. 15, 2000.

FIELD OF THE INVENTION

The present invention generally relates to particle collection and to a method, a kit, and an apparatus for collecting and storing genetic material from biological and other samples. Specifically, the present invention pertains to using a dry solid medium that has a solid matrix for sorbing genetic material thereon and has a preserving substance applied to the matrix.

BACKGROUND OF THE INVENTION

There are numerous techniques, methods and apparatus utilized in the biological field that aid in the collection, storage and transfer of various liquid and solid samples. Generally, in order to perform the analysis, the samples are obtained from a source using a swab or other similar sweeping device. Then, the sample is placed on a slide or other storage mechanism for subsequent analysis.

Medical and other biological samples or specimens are obtained for numerous applications and subsequent analysis of the cellular constituents contained therein. Cellular constituents such as DNA, RNA, proteins, and any other substances are taken for subsequent analysis and tests to determine various diseases and illnesses. Genetic material has been used for the purposes of monitoring and diagnosing genetic diseases and blood-borne parasitic diseases such as malaria. Genetic material can further be used for determining paternity and monitoring other unusual cell populations in blood and other fluids.

Analysis of genetic material can be achieved through numerous techniques and utilize various materials. Generally, these techniques and methods involve the initial collection of the genetic material, storage of the genetic material and then subsequent analysis of the genetic material.

The genetic material can be analyzed through a variety of methods including amplification by the polymerase chain reaction (PCR) (PCR Technology: Principles and Applications for DNA Amplification, H. Erlich (ed), Stockton Press, 1989), genotyping, sequencing (Sanger et al (1977) DNA Sequencing with Chain Terminating Inhibitors Proc.Nat-l.Acad.Sci. 74: 5463), optical density quantitation, Southern and Northern blotting, fluorescent detection, making molecular probes, and cloning (Molecular Cloning: a Laboratory Manual, Sambrook et al., Cold Spring Harbor Laboratory, 1989).

Medical or other biological samples or specimens are "blotted" or otherwise transferred onto Whatman FTA™ or other similar material for subsequent analysis of cellular constituents such as DNA, RNA or proteins for diagnostic purposes or storage of the sample for archiving and subsequent analysis.

Companies such as Cytyc, Inc. (Boxborough, Mass.) currently market a cervical smear apparatus that takes the medical swab and automatically processes it to produce a monolayer of cells on a slide to facilitate optical examination for cancerous and pre-cancerous cellular states. A part of this process involves the formation of the cell monolayer on a track-etched membrane that is then "blotted" onto a standard glass slide for the optical analysis.

Various materials and solid media have been and continue to be utilized to provide a base for performing any desired analysis of the genetic material. Those materials include, for example, filter paper or FTA™-coated materials developed by Flinders University, Australia. In particular, FTA™-coated materials have been successfully utilized for preparing all types of genetic material for subsequent genetic analysis. Based on U.S. Pat. Nos. 5,496,562, 5,756,126, and 5,807,527, it has been demonstrated that nucleic acids or genetic material can be immobilized to a cellulosic-based dry solid medium, support or filter (such as an FTA™ filter). The solid support described is conditioned with a chemical composition that is capable of carrying out several functions: (i) lyse intact cellular material upon contact, releasing genetic material, (ii) enable and allow for the conditions that facilitate genetic material immobilization to the solid support (probably by a combination of mechanical and chaotrophic), (iii) maintain the immobilized genetic material in a stable state without damage due to degradation, endonuclease activity, UV interference, and microbial attack, and (iv) maintain the genetic material as a support-bound molecule that is not removed from the solid support during any down stream processing (as demonstrated by Del Rio et al (1995) BioTechniques. Vol. 20: 970–974).

The usefulness of the FTA™ cellulosic filter material described in U.S. Pat. Nos. 5,496,562, 5,756,126, and 5,807,527 has been illustrated for several nucleic acid techniques such as bacterial ribotyping (Rogers, C & Burgoyne, L (1997) Anal. Biochem. Vol. 247: 223–227), detection of single base differences in viral and human DNA (Ibrahim et al (1998) Anal. Chem. Vol. 70: 2013–2017), DNA databasing (Ledray et al (1997) J. Emergency Nursing. Vol. 23, No. 2: 156–158), automated processing for STR electrophoresis (Belgrader, P & Marino, M (1996) L.R.A. Vol. 9: 3–7, Belgrader et al (1995) BioTechniques. Vol. 19, No. 3: 427–432), and oligonucleotide ligation assay for diagnostics (Baron et al (1996) Nature Biotech. Vol 14: 1279–1282).

Currently, cellular material is applied to FTA™ filter media, and once the cellular material is applied, it forms a spot on the FTA™ filter. From this spot, small punches can be taken; each small punch will have immobilized to it enough nucleic acid or genetic material to facilitate a single downstream process such as a PCR reaction. As the two primers administered to a PCR reaction are presented in solution, it is of no consequence that the cellular nucleic acid template is immobilized to the filter. All amplicon will be formed in solution. Amplicon can then be readily removed from the reaction by aspirating the liquid phase away from the FTA™ solid filter punch.

Genetic material prepared using FTA™-coated materials and FTA™ techniques yield highly purified material bound to the cellulosic base filter for the duration of various subsequent applications and amplification reactions. FTA™-coated base filter materials include, but are not limited to Whatman cellulosic BFC-180, 31-ET, glass microfiber, and any other similar filter materials known to those of skill in the art.

Genetic material can be purified from FTA™-coated material and then eluted from the filter using a combination of water, dilute organic acids such as acetic acid, and elevated temperatures. The released genetic material is a soluble fragment of varying length that is suitable for any manner of amplification and detection methodologies. The elution of the genetic material is important in applications that would not be possible if the genetic material remained bound to the FTA™-coated material. As previously mentioned, FTA™ coating can be done on other filter membrane materials additionally including, but not limited to GF/F, GF/B, QMB, Anopore, alumina, GF/M, magnetic impregnated, meltblown polymerics, and surface modified polymerics. These filter membrane materials can yield superior binding capacity, ease of elution, and extended storage of genetic material.

Biological fluid sample collection generally occurs through numerous techniques. Generally known methods include utilizing a broom-type device, swab, or spatula to obtain the sample. Then, the sample is placed onto a dry solid medium for subsequent analysis. Alternatively, the device used to obtain the sample can already have the dry solid media on it. Once the sample is on the dry solid medium, the dry solid medium can be placed on a slide, placed into a vial, a tube, or other similar apparatus for containing the dry solid medium. One apparatus is disclosed in U.S. Pat. No. 5,143,627. The '627 Patent describes an instrument for collecting a quantitatively measured number of biological cellular particles from suspension in a liquid sample and for transferring the counted collected particles, with an essentially monolayer and uniform distribution, to a viewing screen, typically a microscope slide. The instrument has disposable elements and containers that contact the sample material and accordingly require replacement between the processing of successive samples, to avoid inter-sample contamination.

SUMMARY OF THE INVENTION

In accordance with the present invention, there is provided a method, kit, and apparatus for processing a sample and the cells contained therein. Generally, the method involves upstream processing of a sample to obtain a suspension of cells or virions; applying the processed sample on a matrix that has a preserving substance sorbed to the matrix for protecting the genetic material from degradation; and subsequently analyzing the genetic material.

In one aspect, the present invention provides a method of genetic analysis by:
 a. upstream processing a tissue sample;
 b. applying the processed sample on a matrix, including preserving means sorbed to the solid matrix for protecting the genetic material from degradation, to derive genetic material from the sample; and
 c. analyzing the genetic material.

In another aspect the present invention also provides a kit for genetic analysis including:
 a. upstream processing means for processing a tissue sample; and
 b. a matrix, including preserving means sorbed to the matrix for protecting the genetic material from degradation, for receiving a processed sample.

In another aspect, the present invention provides a method of genetic analysis, wherein the method comprises:
 a. upstream processing of a biological sample;
 b. applying the processed sample to a matrix, including preserving means sorbed to the matrix for protecting the genetic material from degradation, to derive genetic material from the sample; and
 c. analyzing the genetic material.

In another aspect, the present invention provides a method of genetic analysis, wherein the method comprises:
 a. upstream processing of a biological sample to produce a suspension comprising cells comprising genetic material;
 b. applying the suspension to a first solid medium;
 c. contacting the cells on the first solid medium with a second solid medium comprising a matrix, including preserving means sorbed to the matrix for protecting the genetic material from degradation, to derive genetic material from the sample; and
 d. analyzing the genetic material.

In another aspect, the present invention provides a method of isolating and analyzing genetic material, wherein the method comprises:
 a. obtaining a biological sample;
 b. processing the biological sample to obtain one or more cells or virions comprising genetic materal;
 c. applying the sample to a solid medium, wherein the solid medium comprises a matrix having a composition sorbed thereto, wherein the composition comprises:
  i. a weak base;
  ii. a chelating agent; and
  iii. an anionic surfactant or detergent;
 d. lysing the cell or virion and retaining the genetic material with the solid medium;
 e. analyzing the genetic material.

In another aspect, the present invention provides a method of detecting and analyzing genetic material from a biological sample, wherein the method comprises:
 a. obtaining a biological sample comprising a cellular component having one or more cells comprising genetic material;
 b. isolating the cellular component, on a first solid medium, from non-cellular components in the sample;
 c. contacting the cellular component with a second solid medium, wherein the second solid medium comprises a matrix having a composition sorbed thereto, wherein the composition comprises:
  i. a weak base;
  ii. a chelating agent; and
  iii. an anionic surfactant or detergent;
 d. lysing the one or more cells in the cellular component and retaining the genetic material with the second solid medium; and
 e. analyzing the genetic material.

In another aspect, the present invention provides a method of isolating and analyzing genetic material from a biological sample from a mammal, wherein the method comprises:
 a. obtaining a biological sample comprising an organ or a tissue comprising cells comprising genetic material;
 b. dissociating the cells to produce a suspension comprising the cells;
 c. isolating the cells on a first solid medium;
 d. contacting the cells on the first solid medium with a second solid medium, wherein the second solid medium comprises a matrix having a composition sorbed thereto, wherein the composition comprises:
  i. a weak base;
  ii. a chelating agent; and
  iii. an anionic surfactant or detergent;
 d. lysing the cells and retaining the genetic material with the second solid medium;
 e. analyzing the genetic material.

In another aspect, the present invention provides a method of isolating and analyzing genetic material from a non-solid biological sample from a mammal, wherein the method comprises:
 a. obtaining a non-solid biological sample comprising a component of interest, wherein the component contains a cell, a virus, or a combination thereof and wherein the cell or the virus comprises genetic material;

b. isolating the component of interest on a first solid medium;

c. contacting the isolated component of interest on the first solid medium with a second solid medium, wherein the second solid medium comprises a matrix having a composition sorbed thereto, wherein the composition comprises:
  i. a weak base;
  ii. a chelating agent; and
  iii. an anionic surfactant or detergent;

d. releasing the genetic material from the component of interest and retaining the genetic material with the second solid medium;

e. analyzing the genetic material.

In another aspect, the present invention provides a method of isolating and analyzing genetic material, wherein the method comprises:

a. obtaining a sample;

b. processing the sample to produce a suspension comprising cells or virions comprising genetic material;

c. isolating the cells or virions on a first solid medium;

d. contacting the cells or virions on the first solid medium with a second solid medium, wherein the second solid medium comprises a matrix having a composition sorbed thereto, wherein the composition comprises:
  i. a weak base;
  ii. a chelating agent; and
  iii. an anionic surfactant or detergent;

e. lysing the cells or virions and retaining the genetic material with the second solid medium; and f. analyzing the genetic material.

In another aspect, the present invention provides a method of isolating and analyzing genetic material from cells or virions, wherein the method comprises:

a. providing a first solid medium comprising cells or virions comprising genetic material;

b. contacting the cells or virions on the first solid medium with a second solid medium, wherein the second solid medium comprises a matrix having a composition sorbed thereto, wherein the composition comprises:
  i. a weak base;
  ii. a chelating agent; and
  iii. an anionic surfactant or detergent;

c. lysing the cells or virions and retaining the genetic material with the second solid medium; and d. analyzing the genetic material.

In another aspect, the present invention also provides a kit for isolating genetic material, wherein the kit comprises:

a. a first solid medium capable of retaining cells or virions;

b. a second solid medium, wherein the second solid medium comprises a matrix having a composition sorbed thereto, wherein the composition comprises:
  i. a weak base;
  ii. a chelating agent; and
  iii. an anionic surfactant or detergent.

In another aspect, the present invention provides an apparatus for isolating genetic material, wherein the apparatus comprises:

a. a chamber for containing a fluid including a suspension of cells therein, the chamber comprising:
  i. an opening therethrough; and
  ii. a first matrix removably disposed over the opening;

b. vacuum means for drawing the fluid from the chamber and through the first matrix and depositing the cells on the matrix;

c. a second matrix comprising preserving means for lysing cells and preserving genetic material sorbed to the matrix by protecting the genetic material from degradation.

BRIEF DESCRIPTION OF THE DRAWINGS

The FIGURE is a photograph of agarose gel electrophoresis showing detection of as few as $10^3$ cells by swabbing the surface of a membrane with an FTA™ swab followed by amplification by PCR, as described in Example 2.

DETAILED DESCRIPTION OF THE INVENTION

While specific embodiments are disclosed herein, they are not exhaustive and can include other suitable designs, methods and structures. Basically, any differing design, structure, materials, and methods known to those of skill in the art can be utilized without departing from the spirit of the present invention.

As described above, companies, such as Cytyc, Inc. (Boxborough, Mass.), currently market a cervical smear apparatus that takes the medical swab and automatically processes it to produce a monolayer of cells on a slide to facilitate optical examination for cancerous and pre-cancerous cellular states. A part of this process involves the formation of the cell monolayer on a track-etched membrane that is then "blotted" onto a standard glass slide for the optical analysis.

It is envisioned that in this invention, systems such as those of Cytyc, Inc., could be extended to facilitate DNA or other biochemically determined methods of diagnosis. An example would be the direct blotting or "swabbing" of cervical cells from, e.g., a track-etch membrane onto FTA™ paper from which samples could be punched or the DNA eluted for subsequent amplification (e.g., PCR) (if required) and detection of genetic based disease or other conditions. By this example, other factors associated with cervical cancer (e.g., human papilloma virus (HPV) and metastasis conditions) could be detected giving parallel and supplemental information to aid and improve diagnosis.

In the above example, the FTA™ paper may comprise a cellulose matrix, but could also comprise a glass fiber matrix with FTA™ coating. The FTA™ paper could be attached by various means to a platform which has similar dimensions to the standard microscope slide and would be conveniently handled and stored as for normal slide preparations. The slide would of course have features which would allow sample taking for subsequent analysis.

In a preferred embodiment, the analyzing step further includes phenotyping or genotyping the processed tissue sample and cells therein.

In a preferred embodiment, the matrix further comprises:
a. a weak base;
b. a chelating agent;
c. an anionic surfactant or detergent.

In a preferred embodiment, the upstream processing step further includes dissociating the cells of the sample and isolating the cells on a first solid medium distinct from the second solid medium comprising a matrix having a composition sorbed thereto, wherein the composition comprises a weak base, a chelating agent, and an anionic surfactant or detergent.

The genetic material may be, but is not limited to, DNA or RNA, including genomic DNA or mRNA. It may be mammalian genetic material, genetic material proper to the cells of the sample of interest, or genetic material of a parasite, contaminant, or infectious agent. Thus, in one preferred embodiment, the method may further comprise detection of contamination of the sample or of the first solid medium.

The biological sample may be, but is not limited to, blood, plasma, serum, mucus, urine, saliva, sweat, semen, a culture, a fluid sample, water, a food, a beverage, or a non-biological solid.

The present invention has a number of advantages and unexpected features, including the following:
1. It adds greater analytical ability to conventional systems, enabling more diagnoses from the same sample material.
2. It adds a sample storage/archiving feature, allowing easy track back for repeat or historic investigations.
3. It is compatible with existing systems.
4. It can be used with FTA™ systems and similar systems, which are safe and generally non-toxic.
5. "Blotting" or "swabbing" of the sample onto FTA™ materials can be performed after the initial optical slide sample is prepared without contamination or the need to perform two preparations for different diagnostic purposes from the same sample.
6. It can be linked into a multi-sample processing system.
7. It can be adapted for easy automation.
8. It has a wide variety of potential applications, including microbial analysis from foods, beverages, water, and potentially contaminated solids and liquids, such as environmental sources and targets of biohazardous contamination, both by accident or by intentional sabotage.
9. It entails a lower cost per test when used as a common sample preparation method.

The present invention can be used in a variety of settings including, but not limited to the analysis of blood, plasma, sera, urine, tissues, and any other biological material. Further, the present invention can be used in cervical tests, PAP smears, biopsies, detection of metastasis, identification of organisms, detection of genetic mutations, and any other similar testing known to those of skill in the art. The present invention can be used for the microbial analysis of foods, fluid samples and other substances known to those of skill in the art. The invention, however, is not meant to exclude any application outside of the biological and medical fields.

The present invention is best utilized with substances or samples containing DNA, RNA, mRNA, and any other genetic material known to those of skill in the art. Specifically, the present invention is very useful in applications involving mRNA detection. The detection of mRNA is important because it is the only nucleic acid molecule in a cell that gives an indication of the level of gene expression. Thus, the FTA™ coated material used in the present invention has the ability to "bottle" mRNA for subsequent processing, diagnosis, and analysis. Thus, the present invention can be used with animals, plants, or any organism known to those of skill in the art.

The present invention can find utility in many areas of genomics. For example, the present invention provides the capability to elute bound genetic material for the rapid purification of the genetic material to be utilized in any number of forensic applications, such as identification, paternity/maternity identification, and at the scene of a crime.

The present invention can be utilized for paternity or maternity identification having a particular use for a mother or hospital wherein a newborn has been mislaid in the hospital. The rapid ability of the present invention to provide for a purified genetic sample provides even greater utility in such instances where a speedy identification of a mislaid child would be most propitious.

The present invention is a significant contribution to current methodology for the preparation of soluble genetic material which are otherwise time consuming and often result in inadequate template that is damaged or contaminated. The rapidly purified genetic material can be utilized for any number of food and agricultural applications including, but not limited to, tracing, breeding, identification, and cloning.

The use of the present invention in food testing or carcass analysis and archiving allows for rapid isolation and detection for the presence of pathogenic genetic material. Time consuming prior art assay techniques and involved nucleic acid preparations do not need to be performed if the present invention is utilized. Collected pathogenic nucleic acid can be used as a soluble fraction or solid phase fraction with the choice of an elution step.

Tracing carcass material, whether for legal or health issues enables manufacturers to keep control of their products. At the point of kill in a slaughterhouse, the present invention can be used to identify the carcass and provide an archival function at the slaughterhouse. If an identification issue arises for a certain carcass, genetic records on both the carcass and the slaughterhouse can be utilized.

The present invention and any other similar embodiment have several advantages in addition to lower costs. First, the present invention allows for greater analytical ability as compared to conventional systems. Additionally, more diagnostic testing, analysis and other forms of testing known to those of skill in the art can be performed from the same sample material. The present invention can add a sample storage or archiving feature for repeat or historic investigations. Furthermore, blotting or swabbing of a sample onto the present invention can be performed. The present invention can be linked to a multiple processing system, automated system, and adapted to existing systems known to those of skill in the art.

Prisoners from many countries are required to give a genetic sample (blood or buccal sample) for DNA fingerprinting purposes. The use of the present invention provides a means for the long-term storage of prisoner genetic material. If necessary, the genetic material can be tested as soon as it is taken or many years after storage. The genetic material can be obtained as either a soluble or solid phase fraction once isolated on the filter media of the present invention.

Identifying the desired genes and characteristics that are required for a subsequent generation of a plant or animal requires the time effective and reliable generation of nucleic acid from potential parents. The present invention can be used for the isolation of either soluble or solid phase genetic material to provide effective and reliable results in such a need. Likewise, the present invention, in the form of microplates, a tube or a chip, can be used for the generation and detection of genetic material. The present invention provides methodology for superior template preparation time (whether soluble or solid) and cost effective archiving.

The present invention can further be utilized in the areas of purification from a patient's whole blood. Currently, genomic DNA is typically purified from a patient's whole blood, the genetic material present in the leukocyte population. Methods of genomic DNA extraction often involve many steps and involve several buffers and purification matrices. Recently, several new methodologies for genomic DNA extraction have been available. One is the FTA™ 31 ET isolation exploited by Fitzco-Whatman. Another is the method described by Cambridge Molecular Technologies Ltd., UK (CMT), using Whatman F58301 (GFIL) material. The Fitzco-Whatman method utilizes an FTA™ coat on a 31 ET cellulosic material that spontaneously lyses leukocytes releasing the genomic DNA. This promotes integration and binding with the media. The DNA is fixed permanently to the media, as no methodology for elution of DNA from the prior art FTA™ coated 31 ET was determined. For many applications, the fact that the genomic DNA bound to the 31 ET media cannot be eluted poses no problem whatsoever. PCR and RFLP are readily performed on the bound template. However, for genotyping experimental where many PCR reactions are carried on the same DNA population, the invention can be used for the isolation of either soluble or solid phase genetic material to provide effective and reliable results in such a need. Likewise, the present invention, in the form of microplates, a tube or a chip, can be used for the generation and detection of genetic material. The present invention provides methodology for superior template preparation time (whether soluble or solid) and cost effective archiving.

The present invention can further be utilized in the areas of purification from a patient's whole blood. Currently, genomic DNA is typically purified from a patient's whole blood, the genetic material present in the leukocyte population. Methods of genomic DNA extraction often involve many steps and involve several buffers and purification matrices. Recently, several new methodologies for genomic DNA extraction have been available. One is the FTA™ 31 ET isolation exploited by Fitzco-Whatman. Another is the method described by Cambridge Molecular Technologies Ltd., UK (CMT), using Whatman F58301 (GF/L) material. The Fitzco-Whatman method utilizes an FTA™ coat on a 31 ET cellulosic material that spontaneously lyses leukocytes releasing the genomic DNA. This promotes integration and binding with the media. The DNA is fixed permanently to the media, as no methodology for elution of DNA from the prior art FTA™ coated 31 ET was determined. For many applications, the fact that the genomic DNA bound to the 31 ET media cannot be eluted poses no problem whatsoever. PCR and RFLP are readily performed on the bound template.

In accordance with the present invention, there is provided a method, kit, and apparatus for processing a sample, such as a biological sample, and the cells contained therein. Generally, the method involves upstream processing of a sample to produce a suspension comprising cells; isolating the cells on a first matrix; contacting the isolated cells to a second matrix that has a preserving substance sorbed to the matrix for protecting the genetic material; and analyzing the genetic material.

The method further includes the step of genotyping or phenotyping the processed tissue sample and cells therein. The method can also include performing other similar testing known to those of skill in the art. Additionally, the method further includes any processing known to those of skill in the art that dissociates the tissue sample into cells. Thus, genetic material isolated from the media can then be utilized for any manner of diagnostic procedure depending on whether soluble or solid phase genetic material is required. This analysis can be done almost effectively immediately, as opposed to prior art techniques.

The method disclosed herein further includes a method of storing a genetic material most generally including the steps of immobilizing a genetic material on the medium and lysing cells and releasing the genetic material from the lysed cells while stabilizing the immobilized released genetic material.

The chemical composition of the medium facilitates the lysis of whole cells and the subsequent capture of the released nucleic acids. The chemical composition further aids in their long-term storage. The composition of the medium is such that the rapid purification of the captured nucleic acid can be carried out. In some embodiments, the genetic material is retained with the medium; in other embodiments, the medium itself allows for the release of nucleic acid by an elution step thereby providing a soluble nucleic acid fraction.

One embodiment of the present invention is a kit including an upstream processing mechanism for processing the sample and a matrix that has a preserving substance sorbed to the matrix for protecting the genetic material from degradation. The matrix used herein or disclosed in this or any embodiment of the present invention includes, but is not limited to, FTA™ coated materials, filter paper, and any other similar solid medium known to those of skill in the art. The use of the kit first involves obtaining a sample, such as cells from a biological sample, with a device similar to, but not limited to, a cotton swab, spatula, or other similar device known to those of skill in the art. Then, the sample is placed upon a mechanism, structure, platform, or other similar structure known to those of skill in the art. In the preferred embodiment, the platform has dimensions of the standard microscope slide and could be conveniently handled and stored for normal slide preparations. Then, the sample could be transferred to a matrix, the matrix having the preserving substance sorbed thereto. The slide would have features that could allow sample taking for subsequent analysis. The structure, however, does not have to be limited to a sample prep system or slide format. It could apply to most tissue or other biological sample processing and storage procedures where either immediate and/or subsequent diagnostic analysis is required.

The kit can additionally contain various rinses to remove any undesired impurities, protein, or the like. The techniques and the solutions to perform the rinses are known to those of skill in the art. Once placed in the storage structure, it can either be stored for future analysis or immediately used.

Another embodiment of the present invention is an apparatus for processing genetic material and includes a chamber for containing a fluid having a single cell suspension therein; a vacuum mechanism for drawing the fluid from the chamber and through the first matrix and depositing the cells on the first matrix; and a second matrix comprising a preserving substance disposed on the matrix for lysing cells and preserving genetic material sorbed to said matrix by protecting the genetic material from degradation. The apparatus can be a microscopic slide, vial, tube, or any other similar container. The apparatus must be non-reactive with the genetic material and include, but is not limited to, a tube made from a polymer selected from the group consisting of common polypropylene, but also polysulphone.

The device further includes an apparatus or other similar platform for containing or affixing the dry solid medium for convenient handling and storage for normal subsequent preparations and analysis. The coated matrix (to which the sample is transferred) contained in or on the apparatus or platform comprises a solid matrix for sorbing genetic material thereon and a preserving substance sorbed to the solid matrix for protecting the genetic material, applied to the matrix, from degradation.

The medium described and used in the present invention generally includes a matrix for immobilizing a genetic material thereon and allowing subsequent elution of the genetic material therefrom. A coating is functionally associated with the matrix for enabling cellular lysis and in some embodiments (e.g., FTA™ Elute and similar embodiments), releasing the genetic material from the lysed cells while stabilizing the immobilized released genetic material. Preferably, the matrix of the present invention is a porous material in the form of a filter membrane as described and defined below.

The filter membrane is a porous material or filter medium formed, but not limited to, either fully or partly from glass, silica or quartz including their fibers or derivatives thereof. Other materials from which the filter membrane can be composed also include cellulose-based (nitrocellulose or carboxymethylcellulose papers), hydrophilic polymers including synthetic hydrophilic polymers (eg. polyester, polyamide, polycarbonate, carbohydrate polymers), polytetrafluoroethylene, and porous ceramics. Basically, the media used for the filter membrane of the invention includes any material that does not inhibit the sorption of the chemical coating solution and which does not inhibit the storage and subsequent analysis of nucleic acid-containing material added to it. This includes flat dry matrices or a matrix combined with a binder. It is preferred that the filter membrane of the invention be of a porous nature to facilitate capture of nucleic acid.

The chemical coating solution is a chemical composition that is able to sorb to the aforementioned filter membrane. The composition of the chemical coating solution is as described and relates to that outlined in U.S. Pat. Nos. 5,756,126, 5,807,527, and 5,496,562, the disclosures of which are incorporated herein by reference.

More specifically, the chemical coating solution includes a protein-denaturing agent that can be a surfactant that will denature proteins and the majority of any pathogenic organisms in the sample. Anionic detergents are examples of such denaturing reagents. The chemical solution can include a weak base, a chelating agent, and the anionic surfactant or detergent, and optionally uric acid and orate salt as discussed in detail in the above-cited U.S. Pat. No. 5,807,527. More preferably, the weak base can be, but is not limited to, a Tris, trishydroxymethyl methane, either as a free base or as the carbonate, and the chelating agent can be, but is not limited to, EDTA, and the anionic detergent can be, but is not limited to, sodium dodecyl sulfate. Other coatings having similar function can also be utilized in accordance with the present invention.

The chemical coating is disposed, sorbed, or otherwise associated with the matrix of the present invention such that the matrix and coating function together to immobilize nucleic acid thereon through an action of cellular lysis of cells contacted by the matrix. That is, the coating can be adsorbed, absorbed, coated over, or otherwise disposed in functional relationship with the media.

The coated matrix of the solid medium disclosed and described herein for isolating genetic material is a functional solid matrix that enables the specific immobilization of nucleic acid through an action of cellular lysis. Nucleic acid may be presented to it in the form of nucleic acid-containing material such as blood, cultured mammalian cells, saliva, urine, cultured bacterial cells, yeast, solid tissue, feces, lymphatic fluid, amniotic fluid, plant tissue, and the like, which are isolated on a matrix, a swab, a blot, or a similar device as described above.

The coated matrix of the invention is such that nucleic acid immobilized to it can remain so in a stable form, not exhibit degradation, shearing, endonuclease digestion, or UV damage.

The coated matrix of the invention is such that at any point during a storage regime, it allows for the rapid purification of immobilized nucleic acid. In some embodiments of the invention, the immobilized nucleic acid is collected in the form of a soluble fraction following a simplified elution process, during which immobilized nucleic acid is released from the coated matrix of the invention. In embodiments not utilizing an elution step, the coated matrix may be micro-punched, for example, to obtain samples. The coated matrix of the invention yields nucleic acid of sufficient quality that it does not impair downstream analyses such as polymerase chain reaction (PCR), ligase chain reaction (LCR), transcription mediated amplification (TMA), reverse transcriptase initiated PCR, inverse PCR (I-PCR), rapid amplification of cDNA ends (RACE), DNA or RNA hybridization techniques, various types of sequencing, and the like.

Although a suitable template for singular PCR reactions, nucleic acid isolated on a solid matrix cannot be measured or detected by traditional techniques such as optical density or fluorescence. Nucleic acid has to be in solution for these techniques. Other post purification techniques where nucleic acid is desired in the soluble form includes cloning, hybridization protection assay, bacterial transformation, mammalian or other transfection, transcription-mediated amplification, and the like.

The coated matrix of the invention can possess the same chemical component as FTA™ that enables the action of cellular lysis and nucleic acid release upon transfer of the sample. The chemical component ensures nucleic acid stability via protein denaturants, a free radical trap, and viral/microbial inhibitors.

An example of an embodiment allowing elution of the genetic material is FTA™ Elute. This change in solid matrix material, or filter, has enabled, upon a simplified heat elution step, bound nucleic acid to be removed from the filter membrane of the invention whereas it cannot be removed, for example, from FTA™ Classic Card solid matrix (see Del Rio et al. (1995) BioTechniques. Vol. 20: 970–974). For example, the eluting step can be accomplished by heating the medium having the genetic sample immobilized thereon, the medium releasing the heated genetic material therefrom and into solution, preferably into nuclease free water. Most preferably, this is accomplished by disposing the medium having the genetic immobilized thereon into heated water, the water being heated preferably between 65° C. and 100° C.

In embodiments in which the genetic material is eluted, the nucleic acid released from the filter membrane of the invention is presented as a soluble fraction that can be readily aliquoted to multiple downstream processes such as PCR amplification. The eluted soluble nucleic acid can also be entered into techniques where soluble nucleic acid is a necessity such as optical density analysis, fluorescence detection, cloning, transformation, and the like. This added technique of elution enables high throughput multiple processing regimes, such as genotyping.

Various washes can be performed in various types of buffers. Preferably, the washing buffers can be selected from the group including Tris/EDTA; 70% ethanol; STET (0.1 M NaCl; 10 mM Tris-Cl, pH 8.0; 1 mM EDTA, pH 8.0; 5% Triton X-100); SSC (20×SSC=3 M NaCl; 0.3 M sodium citrate; pH 7.0 with NaOH); SSPE (20×SSPE=3 M NaCl; 0.2 M $NaH_2PO_4$—$H_2O$; 0.02 M EDTA; pH 7.4); FTA™ purification reagent, and the like.

"Biological sample" includes samples of tissues, cells, blood, fluid, or other materials obtained from a biological organism. It also includes a biological organism, cell, virus, or other replicative entity. Also included are solid cultures (such as bacterial or tissue cultures). Also included are solid samples, including, but not limited to, food, powder, and other solids, including non-biological solids, containing a biological organism, cell, virus, or other replicative entity. Also included are washing, homogenizations, sonications, and similar treatments of solid samples. Likewise, the term includes non-solid biological samples.

"Non-biological solid samples" include samples from a wide variety of items, including, but not limited to, wood, concrete, dirt, plastics, and any other solids that have the potential to become contaminated.

"Non-solid biological samples" include those that are not a tissue or an organ. Examples include, but are not limited to, blood, plasma, serum, mucus, urine, saliva, or semen. Also included are cultures (such as bacterial or tissue cultures). Also included are fluid samples, including, but not limited to, water and beverages containing a biological organism, cell, virus, or other replicative entity.

Methods of dissociating cells, such as cells in tissues, organs, or multi-cellular organisms, include physical, chemical, and enzymatic methods. Examples include, but are not limited to, mincing, homogenizing, sonicating, and grinding, preferably in a physiological buffer, such as described in this specification or known to those of ordinary skill in the art.

"Nucleic acid" includes DNA and RNA of various types, including genomic DNA and mRNA, and derivatives thereof, including modified DNA or RNA.

EXAMPLE 1

The present invention provides an ideal solution by allowing for elution of the DNA thereby providing a soluble DNA for each of the reactions performed. Specifically, the method utilizes Whatman GF/L glass fiber that has been shown to specifically capture leukocytes from whole blood application. Upon cellular capture, a lysis buffer is introduced and the released genomic DNA binds to the GF/L. The genomic DNA-GF/L binding is a strong enough interaction to withstand several washing steps. After washing, the GF/L bound genomic DNA is eluted with the application of water or TE buffer to the filter at preferably 82° C. As discussed above, a range of temperatures and buffers can be used. The GF/L media ensures leukocyte capture from whole blood. The coating of the present invention promotes lysis of the cells without the addition of inconvenient lysis buffers and steps. The genomic DNA stays bound to the GF/L media during washing steps. Full elution of the bound genomic DNA is achieved with the addition of water or buffer at the appropriate temperature, preferably 80° C.

With the genomic DNA in a soluble format, many PCR reactions can be carried out from the same DNA population with simple aliquoting of the template rather than cumbersome punching. Likewise, a FTA™ coated GF/L matrix can be incorporated into a single tube, as discussed above, of a microplate device depending on the degree of throughput required.

EXAMPLE 2

Use of FTA™ to Detect Cells Collected by Filtration

Purpose:

To determine if FTA™ can be used for the collection of DNA from cells captured on the surface of a filtration membrane.

Method:

Overview: Specific numbers of cells were captured on the surface of a filter membrane, and the cells collected onto a small piece of FTA™ Classic Card. (FTA™ Elute, a glass fiber-based matrix material with FTA™ coating, can also be utilized.) Then, a small punch was made from each piece of FTA™ Classic Card, washed and used as a template for PCR to detect human DNA. The products were identified by gel electrophoresis. This shows what range of cells can be detected using FTA™ in this manner.

Cultured cells of a human leukocyte cell line HL60 (grown as a suspension culture) were counted and the viability determined using Trypan Blue exclusion. The viability of the cells was ≧94%. The cells were then serially diluted in sterile phosphate buffered saline, pH 7.6 (PBS) (10× stock=137 mM NaCl; 2.7 mM KCl; 5.4 mM $Na_2HPO_4$; 1.8 mM $KH_2PO_4$; pH 7.6) for concentrations of $7\times10^2$, $7\times10^4$ and $7\times10^5$ cells/ml. Cells were collected by filtering 10 ml of each concentration through track etch membrane (pore size of 0.2 µm). After the filtration, the cells were trapped on the surface and were collected onto FTA™ by swabbing the surface with a small 3 mm diameter disk of FTA™.

(During this process, the entire surface area of the disk was used and the FTA™ became thoroughly soaked with the trapped cell suspension. It was therefore assumed that the cells had been fairly evenly distributed on the FTA™.)

The disks were allowed to dry for 1 hr and a small punch, 1.2 mm diameter, was taken from each disk using a Harris Micropunch®. The small punch amounted to approximately 1/7 of the 3 mm diameter disk. Therefore, if the cells had been evenly distributed on the FTA™ disk, the respective 1.2 mm punches contained $1\times10^3$, $1\times10^5$, and $1\times10^6$ cells.

Each punch was placed in a PCR tube and washed 3 times with 200 µl FTA™ wash buffer, 5 min./wash, followed by 2 washes with 200 µl $TE^{-1}$ (10 mM Tris-HCl, pH 8.0; 0.1 mM EDTA) for 5 min each. To each punch was added 25 µl of PCR master mix including primers for a 1.3 kb PCR product from the human globin gene. The template DNA was denatured for 3 min. at 95° C. followed by 30 cycles of 95° C. for 1 min, 65° C. for 1 min., 72° C. for 4 min. There was a final extension of 72° C. for 5 min. The products were separated on a 1% agarose gel containing ethidium bromide (0.5 µg/ml) and photographed using a digital imaging system.

Result: The results show that using FTA™, cells can be harvested from the surface of the membrane and detected using PCR.

As shown in the FIGURE, as few as $10^3$ cells can be detected by swabbing the surface of a membrane with FTA™ followed by amplification by PCR. M=DNA ladder used to determine the size of the bands. +Con=positive PCR control (human genomic DNA used as template); −Con= negative PCR control, no template added to the reaction. The approximate number of cells on each 1.2 mm FTA™ punch taken from the 3 mm diameter disks is indicated (ranging from $10^3$ to $10^6$). Note that the PCR product for the lowest cell number gave the cleanest product.

Throughout this application, various publications, including United States patents, are referenced by author and year and patents by number. Full citations for the publications are listed below. The disclosures of these publications and patents in their entireties are hereby incorporated by reference into this application in order to describe more fully the state of the art to which this invention pertains.

The invention has been described in an illustrative manner, and it is to be understood that the terminology, which has been used, is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A method of genetic analysis, wherein the method comprises:
   a. upstream processing of a biological sample to produce a suspension comprising cells comprising genetic material;
   b. applying the suspension to a first solid medium;
   c. contacting the cells on the first solid medium with a second solid medium, wherein the second solid medium is a dry solid medium comprising:
      i. a matrix; and
      ii. a composition sorbed to the matrix, the composition comprising preserving means for protecting genetic material from degradation;
   d. sorbing the genetic material to the second solid medium; and
   e. analyzing the genetic material.

2. The method of claim 1, wherein the analyzing step further includes phenotyping the processed biological sample and cells therein.

3. The method of claim 1, wherein the preserving means comprises:
   a. a weak base;
   b. a chelating agent;
   c. an anionic surfactant or detergent.

4. The method of claim 1, wherein the upstream processing step further includes dissociating the cells of the biological sample.

5. The method of claim 1, wherein
   a. the biological sample comprises an organ, a tissue, or a multi-cellular organism or colony; and
   b. the processing step a further comprises dissociating cells in the biological sample.

6. The method of claim 1, wherein the genetic material comprises DNA or RNA.

7. A method of analyzing genetic material, wherein the method comprises:
   a. obtaining a biological sample;
   b. processing the biological sample to obtain one or more cells or virions comprising genetic material, wherein the processing step comprises:
      i. dissociating cells in the biological sample to produce a suspension; and
      ii. isolating a cell or virion on a first solid medium;
   c. applying the cell or virion isolated on the first solid medium to a second solid medium, wherein the second solid medium is a dry solid medium comprising a matrix having a composition sorbed thereto, wherein the composition comprises:
      i. a weak base;
      ii. a chelating agent; and
      iii. an anionic surfactant or detergent;
   d. lysing the cell or virion and retaining the genetic material with the second solid medium;
   e. analyzing the genetic material.

8. A method of detecting and analyzing genetic material from a biological sample, wherein the method comprises:
   a. obtaining a biological sample comprising a cellular component having one or more cells comprising genetic material;
   b. isolating the cellular component, on a first solid medium, from non-cellular components in the sample;
   c. removing non-cellular components;
   d. contacting the cellular component with a second solid medium, wherein the second solid medium is a dry solid medium comprising a matrix having a composition sorbed thereto, wherein the composition comprises:
      i. a weak base;
      ii. a chelating agent; and
      iii. an anionic surfactant or detergent;
   e. lysing the one or more cells in the cellular component and retaining the genetic material with the second solid medium; and
   f. analyzing the genetic material.

9. The method of claim 8, wherein the biological sample comprises blood, plasma, serum, mucus, urine, saliva, sweat, or semen.

10. The method of claim 8, wherein the biological sample comprises a culture, a fluid sample, water, a food, a beverage, or a non-biological solid.

11. The method of claim 8, wherein the genetic material comprises DNA or RNA.

12. The method of claim 8, wherein the genetic material comprises genomic DNA or mRNA.

13. A method of detecting and analyzing genetic material from a biological sample from a mammal, wherein the method comprises:
   a. obtaining a biological sample comprising an organ or a tissue comprising cells comprising genetic material;
   b. dissociating the cells to produce a suspension comprising the cells and one or more non-cellular components;
   c. isolating the cells on a first solid medium;
   d. removing substantially all the non-cellular components;
   e. contacting the cells on the first solid medium with a second solid medium, wherein the second solid medium is a dry solid medium comprising a matrix having a composition sorbed thereto, wherein the composition comprises:
      i. a weak base;
      ii. a chelating agent; and
      iii. an anionic surfactant or detergent;
   f. lysing the cells and retaining the genetic material with the second solid medium; and
   g. analyzing the genetic material.

14. The method of claim 13, wherein the genetic material comprises mammalian DNA or RNA.

15. The method of claim 13, wherein the genetic material comprises DNA or RNA from non-mammalian cells or from viruses.

16. A method of detecting and analyzing genetic material from a non-solid biological sample from a mammal, wherein the method comprises:
   a. obtaining a non-solid biological sample comprising a component of interest, wherein the component contains a cell, a virus, or a combination thereof and wherein the cell or the virus comprises genetic material;
   b. isolating the component of interest on a first solid medium and removing substantially all of the remaining components of the sample;
   c. contacting the isolated component of interest on the first solid medium with a second solid medium, wherein the second solid medium is a dry solid medium comprising a matrix having a composition sorbed thereto, wherein the composition comprises:
  i. a weak base;
  ii. a chelating agent; and
  iii. an anionic surfactant or detergent;
d. releasing the genetic material from the component of interest and retaining the genetic material with the second solid medium;
e. analyzing the genetic material.

17. The method of the claim 16, wherein the genetic material comprises DNA or RNA.

18. A method of isolating and analyzing genetic material, wherein the method comprises:
  a. obtaining a sample;
  b. processing the sample to produce a suspension comprising cells or virions comprising genetic material;
  c. isolating the cells or virions on a first solid medium and removing substantially all of the remaining components of the sample;
  d. contacting the cells or virions on the first solid medium with a second solid medium, wherein the second solid medium is a dry solid medium comprising a matrix having a composition sorbed thereto, wherein the composition comprises:
    i. a weak base;
    ii. a chelating agent; and
    iii. an anionic surfactant or detergent;
  e. lysing the cells or virions and retaining the genetic material with the second solid medium; and
  f. analyzing the genetic material.

19. The method of claim 18, wherein the sample comprises one of the following: an organism, an organ, a tissue, blood, plasma, serum, mucus, urine, saliva, sweat, or semen.

20. The method of claim 18, wherein the sample comprises a culture, a fluid sample, water, a food, a beverage, or a non-biological solid.

21. The method of claim 18, wherein the analysis of genetic material includes genotyping.

22. The method of claim 18, further comprising:
  g. detecting contamination of the sample.

23. The method of claim 18, wherein the genetic material comprises DNA or RNA.

24. The method of claim 18, wherein the genetic material comprises genomic DNA or mRNA.

25. A method of detecting and analyzing genetic material from a biological sample, wherein the method comprises:
  a. obtaining a biological sample;
  b. processing the biological sample to produce a suspension of one or more cells or virions comprising genetic material and one or more non-cellular or non-viral components;
  c. providing an apparatus comprising:
    i. a chamber for containing a fluid including a suspension of cells or virions therein, the chamber comprising:
      an opening therethrough; and
      a first solid medium removably disposed over the opening;
    ii. vacuum means for drawing the fluid from the chamber and through the first solid medium and depositing the cells or virions on the first solid medium;
    iii. a second solid medium wherein the second solid medium is a dry solid medium comprising:
      a matrix; and
      a composition sorbed to the matrix, the composition comprising preserving means for protecting the genetic material from degradation;
  d. placing a fluid comprising the suspension in the chamber;
  e. using the vacuum means to draw the fluid from the chamber and through the first solid medium and to deposit the cells or virions on the first solid medium and to remove substantially all of the non-cellular and non-viral components;
  f. contacting the cells or virions on the first solid medium with the second solid medium;
  g. releasing the genetic material from the cells or virions and retaining the genetic material with the second solid medium; and
  h. analyzing the genetic material.

26. The method of claim 25, wherein the preserving means comprises an anionic surfactant or detergent.

27. The method of claim 26, wherein the preserving means further comprises:
  a. a weak base; and
  b. a chelating agent.

28. The method of claim wherein the biological sample comprises blood, plasma, serum, mucus, urine, saliva, sweat, or semen.

29. The method of claim 25, wherein the biological sample comprises a culture, a fluid sample, water, a food, a beverage, or a non-biological solid.

30. The method of claim 25, wherein the analysis of genetic material includes genotyping.

31. The method of claim 25, further comprising:
  i. detecting contamination of the sample.

32. The method of claim 25, wherein the genetic material comprises DNA or RNA.

33. The method of claim 25, wherein the genetic material comprises genomic DNA or mR.NA.

* * * * *